(12) United States Patent
Wiki et al.

(10) Patent No.: US 7,285,789 B2
(45) Date of Patent: Oct. 23, 2007

(54) OPTICAL DEVICE FOR SURFACE-GENERATED FLUORESCENCE

(75) Inventors: Max Wiki, Ecublens (CH); Johannes Edlinger, Feldkirch (AT)

(73) Assignee: OC Oerlikon Balzers AG, Balzers (LI)

( * ) Notice: Subject to any disclaimer, the term of this patent is extended or adjusted under 35 U.S.C. 154(b) by 171 days.

(21) Appl. No.: 10/860,243

(22) Filed: Jun. 3, 2004

(65) Prior Publication Data
US 2005/0051733 A1   Mar. 10, 2005

Related U.S. Application Data

(60) Provisional application No. 60/476,579, filed on Jun. 6, 2003.

(51) Int. Cl.
*G01N 21/00* (2006.01)
*G01J 1/58* (2006.01)

(52) U.S. Cl. ............................. 250/453.11; 250/458.1

(58) Field of Classification Search .......... 250/453.11, 250/458.1, 159.14, 368, 338.4, 483.1, 461.1, 250/484.5, 365
See application file for complete search history.

(56) References Cited

U.S. PATENT DOCUMENTS

| | | | | | |
|---|---|---|---|---|---|
| 3,604,927 | A | * | 9/1971 | Hirschfeld | 250/483.1 |
| 4,263,061 | A | * | 4/1981 | Fatuzzo et al. | 148/276 |
| 4,284,897 | A | * | 8/1981 | Sawamura et al. | 250/461.2 |
| 4,558,012 | A | * | 12/1985 | Nygren et al. | 436/501 |
| 4,649,280 | A | * | 3/1987 | Holland et al. | 250/483.1 |
| 4,659,931 | A | * | 4/1987 | Schmitz et al. | 250/338.4 |
| 4,703,182 | A | * | 10/1987 | Kroneis et al. | 250/458.1 |
| 4,820,649 | A | * | 4/1989 | Kawaguchi et al. | 436/501 |
| 5,006,716 | A | * | 4/1991 | Hall | 250/458.1 |
| 5,082,629 | A | * | 1/1992 | Burgess et al. | 422/82.11 |
| 5,091,653 | A | * | 2/1992 | Creager et al. | 250/484.5 |
| 5,095,213 | A | * | 3/1992 | Strongin | 250/459.1 |
| 5,296,700 | A | * | 3/1994 | Kumagai | 250/216 |
| 5,381,224 | A | * | 1/1995 | Dixon et al. | 356/72 |
| 5,504,336 | A | * | 4/1996 | Noguchi | 250/458.1 |
| 5,552,272 | A | * | 9/1996 | Bogart | 435/6 |
| 5,600,172 | A | * | 2/1997 | McDevitt et al. | 257/436 |
| 5,631,171 | A | * | 5/1997 | Sandstrom et al. | 436/518 |
| 5,646,411 | A | * | 7/1997 | Kain et al. | 250/458.1 |
| 5,672,880 | A | * | 9/1997 | Kain | 250/458.1 |
| 5,780,857 | A | * | 7/1998 | Harju et al. | 250/458.1 |
| 5,841,143 | A | * | 11/1998 | Tuma et al. | 250/458.1 |

(Continued)

FOREIGN PATENT DOCUMENTS

FR      2827959 A1     1/2003

(Continued)

*Primary Examiner*—David Porta
*Assistant Examiner*—Faye Boosalis
(74) *Attorney, Agent, or Firm*—Pearne & Gordon LLP

(57) ABSTRACT

A sample substrate adapted for use with electromagnetic excitation light includes a base and a layer system. The layer system includes a multilayer interference coating with at least two layers wherein the thicknesses of the layers ensure that light emitted by a fluorescent sample material disposed on top of said multilayer interference coating is reflected. Light directed to a fluorescent sample material disposed on the substrate causes light to be emitted from the sample. The layer system includes a multilayer interference coating with at least two layers wherein thicknesses of the layers cause separation of the excitation light from the emitted light.

31 Claims, 6 Drawing Sheets

U.S. PATENT DOCUMENTS

| | | | |
|---|---|---|---|
| 5,847,400 A * | 12/1998 | Kain et al. | 250/458.1 |
| 5,864,146 A * | 1/1999 | Karellas | 250/581 |
| 6,008,892 A * | 12/1999 | Kain et al. | 356/246 |
| 6,117,529 A * | 9/2000 | Leising et al. | 428/209 |
| 6,274,384 B1 * | 8/2001 | Starzl et al. | 436/518 |
| 6,346,376 B1 * | 2/2002 | Sigrist et al. | 435/5 |
| 6,406,802 B1 * | 6/2002 | Arai et al. | 428/690 |
| 6,472,671 B1 * | 10/2002 | Montagu | 250/458.1 |
| 6,492,133 B1 * | 12/2002 | Wickert et al. | 435/34 |
| 6,503,711 B1 * | 1/2003 | Krull et al. | 435/6 |
| 6,867,900 B2 * | 3/2005 | Weisbuch et al. | 359/321 |
| 6,895,077 B2 * | 5/2005 | Karellas et al. | 378/98.3 |
| 6,979,499 B2 * | 12/2005 | Walck et al. | 428/690 |
| 6,982,431 B2 * | 1/2006 | Modlin et al. | 250/573 |
| 2002/0171045 A1 * | 11/2002 | Perraut et al. | 250/458.1 |
| 2002/0182716 A1 | 12/2002 | Weisbuch et al. | |

FOREIGN PATENT DOCUMENTS

| | | |
|---|---|---|
| WO | 0248691 A1 | 6/2002 |
| WO | 03025553 A2 | 3/2003 |

\* cited by examiner

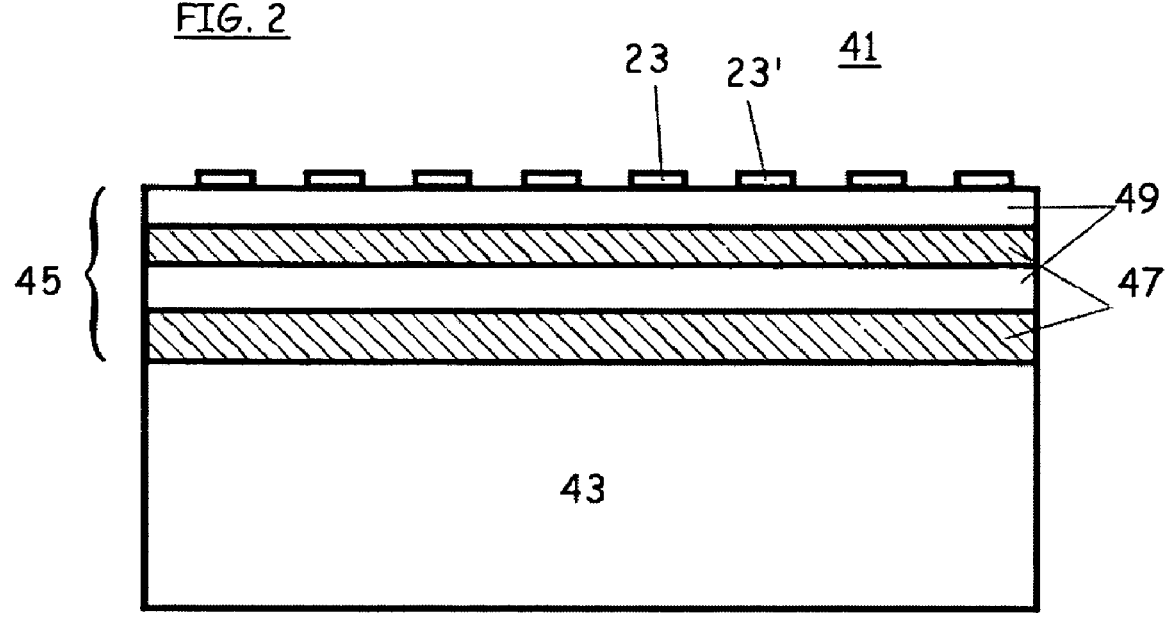

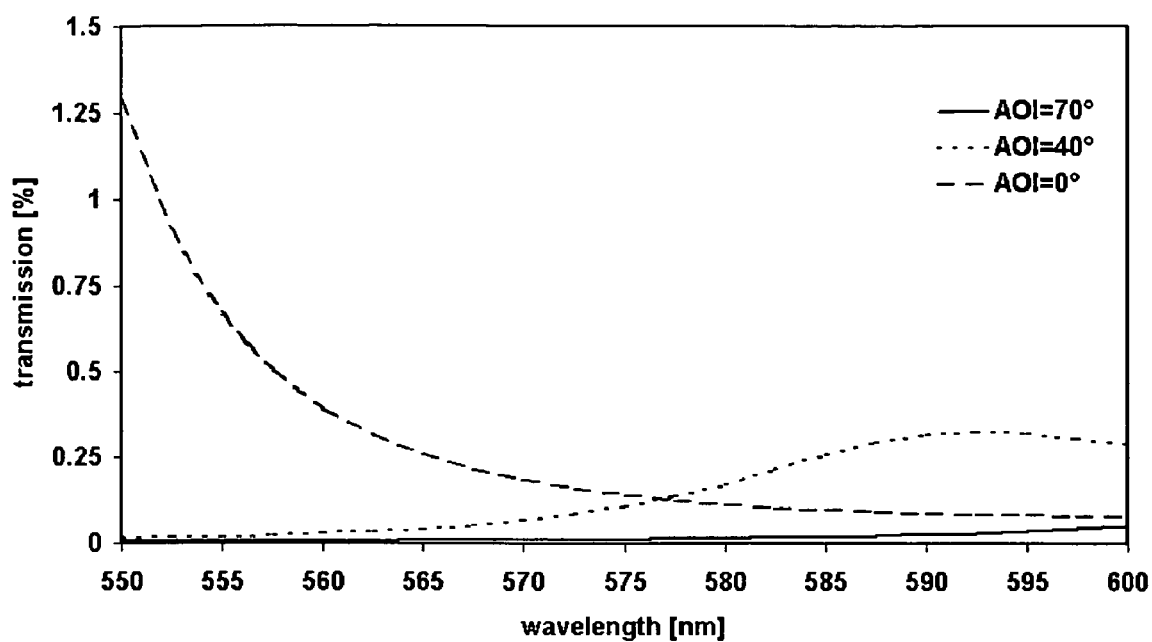

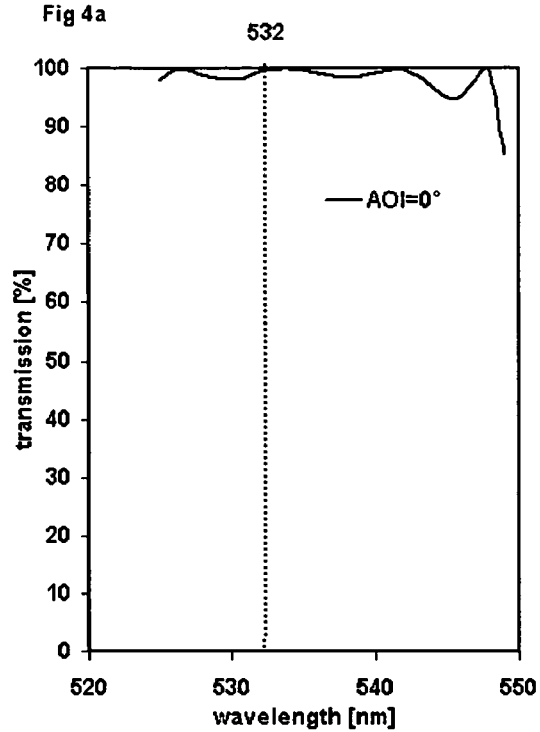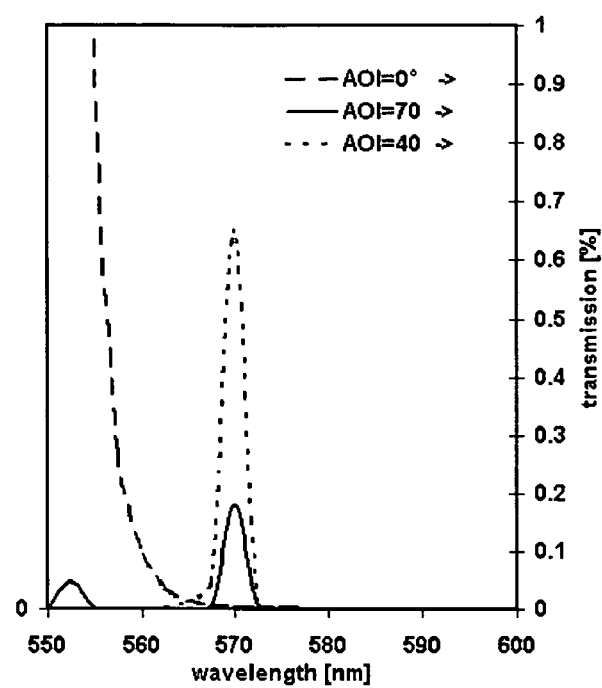

OPTICAL DEVICE FOR SURFACE-GENERATED FLUORESCENCE

FIELD OF THE INVENTION

The present invention relates to a process for amplifying a electromagnetic signal emitted by an areal sample supported by a support in response to an excitation signal. It also relates to a device amplifying the electromagnetic signal emitted by such a sample.

PRIOR ART

Measurement by fluorescence, phosphorescence and luminescence is a method of measurement used in many technical fields. It is used particularly to operate devices of chemical and/or biological analysis often referred to as bio-chips. Measuring biological activity with a chip of this kind is done by measuring an emitted electromagnetic signal in form of fluorescence, phosphorescence or luminescence emission of a molecule fixed to the biological sample, which is presented in the form of a surface coating, using for example an epifluorescence microscope, a scanner, a fluorimeter. Throughout this disclosure the emitted electromagnetic signal will be referred to as emitted light.

To perform the measurement, the chip may be placed in a special chamber or cartridge. It may also be placed directly on the bottom of a Petri dish or a microtiterplate. It may as well be placed in the air using a mechanical support.

In some cases, the areal sample is read in the so-called rear surface mode, which means that the emitted light passes though the support of the area sample before it is collected for detection. In this case the support is necessarily transparent to the emitted light. Alternatively, the areal sample can be read in the so-called front surface mode, which means that the emitted light is not passing through the support of the areal sample before being collected for detection. In this case the support is not necessarily transparent to the emitted light.

As for the emitted light, there is as well a rear surface mode and a front surface mode for the excitation light: The excitation light can be directed towards the areal sample surface through its support in the rear surface mode, or, in the front surface mode, the excitation light can be directed onto the areal sample without transmitting through the support.

Other possibilities to establish an electromagnetic field for exciting fluorescence are to generate evanescent fields for example by total internal reflection or based on waveguides or with grating structures, i.e. resonant grating structures.

The fluorescence readout scheme of microarrays, often uses front surface excitation under nearly normal incidence and front surface readout using objectives with a high numerical apertures as is described in Mark Schena, "*Microarray Analysis*", John Wiley & Sons, Haboken, N.J., 2002.

The areal sample may comprise a biospecific surface formed on at least one surface of the support and acting as a capture phase to a body carrying a fluorescent marker. The biospecific surface may be made by a combinatorial synthesis of probes, by depositing probes using a projection technique or in a different way, various methods are known to the one skilled in the art. It is thus possible to form a complex, for example a nucleic acid duplex. This complex may also be an antibody-antigen association, the antibodies deposited on the surface of the support forming the biospecific surface. The thickness of the surface forming the complex is between a few nanometers and a few hundred nanometers. The complex may also be brought onto the surface after its formation, for example by drying or adsorption of the complex on the support surface.

One of the early documents to mention of the possibility of obtaining an enhancement of fluorescence is an article entitled "*Model for Raman and fluorescent scattering by molecules in small particles*" by H. CHEW et al. *Physical Review A*, 13(1), pp 396 to 404, 1976. This article, which deals simultaneously with Raman scattering and fluorescence, discribes a theoretical model which establishes that the field irradiated by a fluorescent molecule is not isotropic when it is placed in a spherical body (cell, aerosol drop). The theoretical model describes only the angular distribution of light emission but does not conclude on the possibility of applying this principle in order to obtain greater sensitivity.

A detailed description of the fluorescence emission close to surfaces is given in E. H. Hellen et al., "*Fluorescence emission at dielectric and metal-film interfaces*", *J. Opt. Soc. Am.* B, Vol. 4, No. 3, p. 337 (1987). In this article the angular emission characteristic of fluorescent molecules close to surfaces is calculated. The model postulates that for fluorophores very near to bare glass, much emitted light is directed toward the glass at angles near or greater than the critical angle of total reflection, with a sharp peak at the critical angle. In the discussion it is pointed out that the observation of the emission through the glass is better than the direct observation. An objective with a high numerical aperture of 1.4 is proposed for efficient light collection. Further a scheme for selectively collecting the light emitted by molecules close to the surface is given by masking any emission with an angle less than the critical angle.

A further realization of this method based on the emission characteristic is described in J. Enderlein et al., "*Highly efficient optical detection of surface-generated fluorescence*", *Applied Optics*, Vol. 38, No. 4, p. 724, (1999).

Another method for efficiently collecting the light close to the critical angle is described in Lubos Polerecky, "*Theory of the radiation of Dipoles placed within a mulitlayer system*", *Applied Optics*, Vol. 39, No. 22, p. 3968 (2000). One disadvantage of the device described by Polerecky is the requirement special edge finish of the support.

All optical readout schemes for improved fluorescent signals as described before require special rear-surface readout optics. For front surface readout it is not possible to use these optical schemes because light is predominantly propagating along the critical angle within the high index support as already described.

The review on the phenomena of molecular fluorescence near interfaces which was given by R. R. CHANCE et al. in "*Molecular fluorescence and energy transfer near interfaces*", *Advanced in Chemical Physics*, vol XXXVII, pp 1 to 65—Prigogine I., Rice S. R., 1978 is not very helpful in this context because only the phenomena of ionized molecule relaxation time and variations in apparent quantum yields are addressed. A calculation model is presented for dielectric stacks. However this as well only relates to the phenomena of ionized molecule relaxation time and variations in apparent quantum yields.

D. A. WEITZ et al., in an article entitled "*The enhancement of Raman scattering, resonance Raman scattering and fluorescence from molecules adsorbed on a rough silver surface*", *Journal of Chemical Physics*, 79(9), pp 5324 to 5338, 1983, propose a model well adapted to the fluorescence emission of molecules deposited on a rough surface or on a plane surface on which islands of colloidal silver have been deposited. Experiments have been conducted and fully validate the model. The layout investigated only allows for a front surface reading scheme. The effect is described as an electromagnetic coupling between a plasmon resonance on the surface of the colloidal silver to create a very intense local electromagnetic field and the fluorescent molecules. The gain in fluorescence is then a function of the position of the molecules relative to the islands of silver. However there are as well effects inhibiting fluorescence if the molecules are adsorbed on the surface as decribed by K. SOLOKOV et al., entitled "*Enhancement of molecular fluorescence near the surface of colloidal metal film*", Analytical Chemistry, Vol. 70, No 18, pp 3898 to 3905, Sep. 15, 1998.

In WO-A-99/23 492 Zanzucchi et al. disclosed a technique for amplifying fluorescence which makes use of a surface likely to enhance fluorescence. This surface is interposed between a support and the biological complex deposited on the support. The measurement being taken through the support. This intermediate surface must however be textured and, to this end, the material forming this surface is chosen from among nylon membranes, material and texture causing the scattering of the fluorescence signal.

In U.S. Pat. No. 5,822,472 Neuschäfer et al. disclosed a process for detecting luminescence excited evanescently. The process uses a transparent substrate supporting a transparent layer forming a wave guide for the excitation light. The transparent layer material has a refractive index greater than the refractive index of the transparent substrate material. Substances in contact with the waveguide and having luminescent properties are then excited in the evanescent field of the waveguide. The emitted light then passes through the transparent substrate. The transparent layer forming the waveguide has a thickness smaller than the wavelength of the excitation light. Its refractive index is 1.8. Guiding the beam via the transparent layer necessarily entails a loss of part of the fluorescence signal.

In U.S. Pat. No. 6,008,892 Kain et al. disclosed a substrate with a reflective surface which is coated with a transparent layer. The structure is illuminated with narrow linewidth excitation light and by selecting the proper thickness of the transparent layer, an antinode is generated on the surface. By placing the fluorescent sample near the antinode of the excitation light, maximum fluorescence occurs. A disadvantage of this method is that one device can not be optimized for the use of two or more fluorohores at the same time without compromise, since the thickness of the transparent is different for each excitation wavelength. Further the excitation light that is reflected back can increase the background.

In Patent Application U.S. No. 2002/0171045 Chaton et al. use a transparent substrate which is coated with a high index layer or a stack comprising a high index layer for enhancing the fluorescent signal. Molecules placed on a surface which constitutes a discontinuity in the refractive index generally emit the greater part of their fluorescence in the medium which has the highest index. The high index coating, is used in this case to increase the part of the fluorescent light that is emitted into the substrate. Therefore this approach is limited to rear surface readout schemes.

To summarize, prior art solutions for improvement of signal and/or signal/background values in fluorescence measurements are based on rear surface readout requiring special adapted and expensive readout optics or are based on effects involving metallic materials with the drawback of minor stability and minor reproducibility and not allowing for use of transmission effects or involve waveguide or resonant effects which are difficult to realize, require well defined illumination and often show losses due to tight tolerances and purity requirements It is the goal of the present invention to propose a new technique to obtain enhancement of the emitted light and/or improving the signal/background ratio avoiding the drawbacks of the prior art as listed above.

SUMMARY OF THE INVENTION

This objective can be met with a sample substrate which comprises an intermediate dielectric layer system between the support and the areal sample where the intermediate dielectric layer system fulfills specific spectral requirements.

In a first embodiment of the present invention the intermediate dielectric layer system is designed in such a way that, for front surface readout, the emitted light propagating to the support is efficiently reflected by the intermediate dielectric layer system for a broad angular range, preferably comprising the critical angle of total internal reflection. As a consequence most of the emitted light originally propagating into the support is reflected back to the front surface and at least part of the reflected light transmitts and can be collected.

Light, when propagating above the critical angle, undergoes total internal reflection when reflected back to the front surface by the dielectric intermediate layer system. If possible this results in waveguiding. In a preferred embodiment of the present invention at least part of the emission into directions equal to or above the critical angle of total reflection is prohibited. This is the case if the layer thicknesses are chosen in such a way that no waveguiding is possible, as our investigations showed. In other words our investigations showed that this at least partial prohibition can be realized if the layers or layer stacks used to form the intermediate layer system do not allow for waveguiding the emitted light.

In another embodiment of the present invention the intermediate layer system is designed to efficiently separate the excitation light from the emitted light thereby increasing the signal/background ratio.

In the case of front surface excitation and rear surface readout, the intermediate layer system needs to be designed to reflect the excitation light and to transmit the emitted light efficiently.

In the case of front surface excitation and front surface readout the intermediate layer system needs to be designed in such a way that the excitation light is transmitted through the intermediate layer system whereas the emitted light is reflected according to the first embodiment of the present invention. In the case of rear surface excitation the intermediate layer system needs to be designed in such a way that it efficiently transmits the excitation light. In this case in order to separate excitation light from emitted light rear surface readout is applied and the intermediate layer system is designed in such a way that it transmits the emitted light efficiently.

In order to optimize the layout of the dielectric intermediate layer well known optical thin film design tools can be applied. In the following a detailed description of the present invention and a number of preferred embodiments are described with the help of the drawings.

BRIEF DESCRIPTION OF THE SEVERAL VIEWS OF THE DRAWING

FIG. 2 shows a schematic layout of a substrate and samples according to the invention;

FIG. 3 shows a graph of a calculated transmission spectrum of an intermediate layer system;

FIGS. 4a and 4b show calculated transmission spectra for an intermediate multilayer stack optimized for efficient light collection for Cy3 dye and efficient transmission of the excitation wavelength of 532 nm;

FIG. 4a indicates transmission of a wavelength interval around an excitation wavelength for normal incidence coming from air;

FIG. 4b shows transmission of excited light for three different angles of incidence;

DETAILED DESCRIPTION OF THE PRESENT INVENTION

Figure 1:
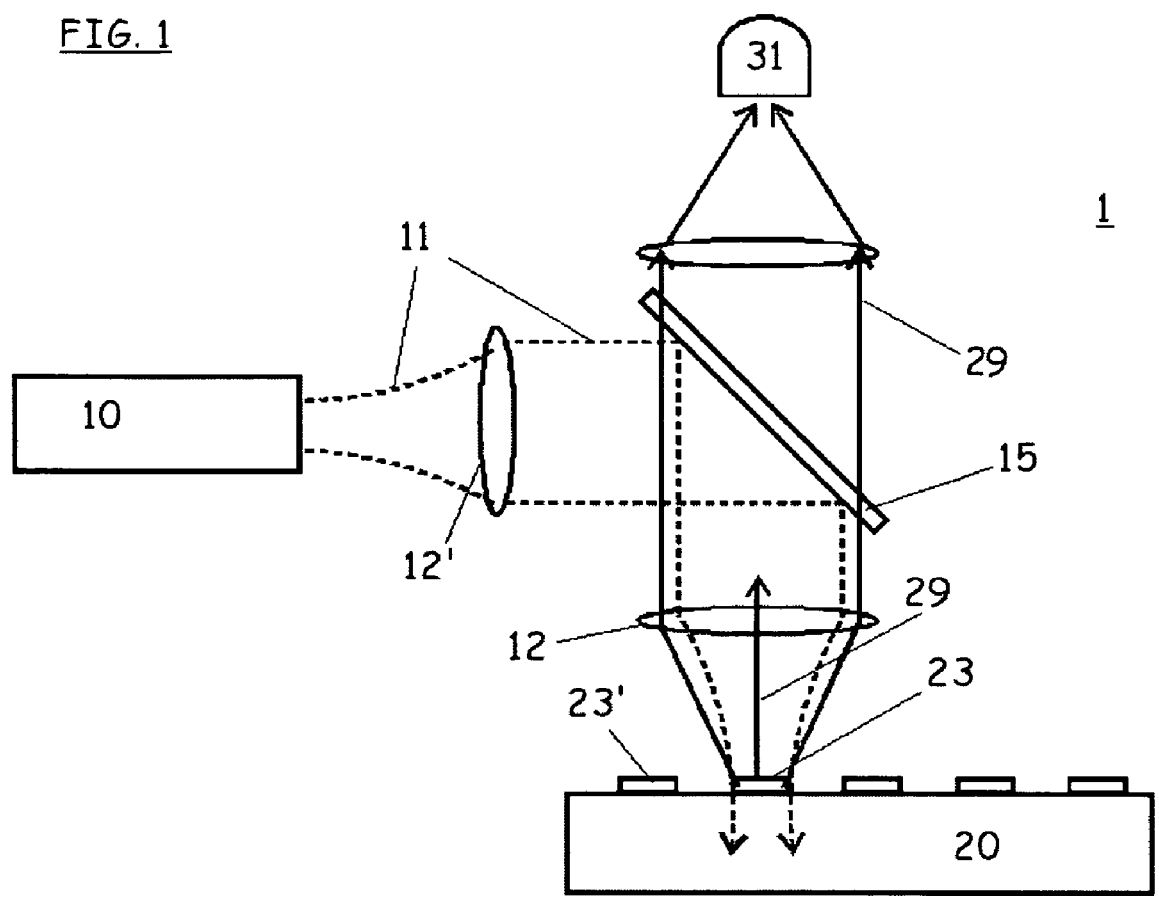
FIG. 1 shows a laser scanner.

In the first example reading the fluorescence signal, a sample substrate is to be placed in a laserscanner, as illustrated in FIG. 1:

A light source 10, such as for example a laser, produces an stimulating beam 11. The stimulating beam 11 is preferably a collimated beam of monochromatic coherent light. However, a noncoherent source, such as a light emitting diode (LED) could be used and a noncollimated source could be coupled to collimating optics to create a collimated beam. If the stimulating beam 11 is not monochromatic, it may be directed through a filter to reduce any unwanted wavelengths.

The stimulating beam 11 is then directed through lens systems 12, 12' and a beam splitter 15 onto the surface of the sample substrate 20. Any scanning mechanism that produces a two-dimensional scan may be used to move the substrate along orthogonal axis in plane with the surface of the sample substrate.

The lens system 12 provides coaxial illumination of the sample substrate with the stimulating beam 11. The stimulating beam 11 is an excitation beam that stimulates fluorescent light emission from the sample substrate 20 at the illuminated spot: If there are areal fluorescent samples 23, 23' on the illuminated surface of the sample substrate stimulation of detectable fluorescent light results. The lens system 12 provides as well coaxial collection of the resulting fluorescent light and a fluorescent light beam 29 is formed. To maximize collection efficiency, it is preferred that the lens system 12 has a high numerical aperture. The fluorescent light is then collected by the lens system 12, acting as a condenser, and directed as a retro-beam back along the incident light path (but in the opposite direction). Since the fluorescent light generally consists of a broad band of wavelengths different from the wavelength(s) of the incident stimulating beam, and since the system should be designed to work with a variety of fluorochromes, the system is preferably largely achromatic and provides correction of chromatic aberrations over a range of wavelengths. Light passing through the lens system 12 impinges upon a photodetector 31, such as a photomultiplier tube (PMT).

This is a scanner based on front surface excitation at nearly normal incidence and front surface light collection using a microscope objective with a high numerical aperture.

FIG. 2 shows a schematic layout of the sample substrate according to the present invention. The sample substrate 41 comprises a support 43 and a number of areal samples 23, 23'. The support 43 can be made of transparent or opaque material. Typically a planar transparent glass or plastic support is used. Alternatively other materials such as metals or opaque plastics and ceramics can be used. The support 43 is coated with an intermediate layer system 45. Preferably the intermediate layer system comprises a number of dielectric layers the refractive index from one layer to the neighboring layer changing from high to low or vice versa. High refractive index materials include $Ta_2O_5$, $TiO_2$, $Nb_2O_5$, $ZrO_2$, ZnO or $HfO_2$. Low refractive index materials include $SiO_2$, MgF and LiF. On top of the intermediate layer system, the specific fluorescent sample can be applied. Preferably, the last layer of the intermediate layer system is a chemically reactive material for binding the specific biological sample thereto.

In order to design such an intermediate layer system it is assumed that the excited light is propagating in a cover medium with an index of refraction similar to the index of the areal sample 23. In the present example this corresponds to the linker chemistry with index n=1.4. This light impinges on the intermediate layer system 45 which is coated on the support 43. The different spectral charactersitics can be realized as required for the different embodiments of the present invention In a first embodiment of the present invention the focus is on front surface readout and efficiently collecting the emitted light. Sample Parameters for efficient light collection are:

Emission wavelength for Cy3-Dye: 550 nm-600 nm (typical fluorescence filter)

Reflective for the emission wavelength for angles of −70° . . . 70°; especially around the critical angle: 40° . . . 60° (s-polarization and/or p-polarization)

FIG. 3 shows the calculated transmission spectrum of an intermediate layer system 45 optimized for efficent light collection in s-polarization for Cy3-Dye. The index of the medium of incidence is supposed to be n=1.4 according to the index of linker chemistry. As can be seen for all angles of incidence from −70° to +70° less than 1.5% is transmitted through the intermediate layer system from the linker medium to the support. The corresponding design of the multilayer stack is listed in table 1. Since no waveguiding is possible within this multilayer stack, emission of fluorescent light in the direction to the support 43 in directions above the critical angle is therefore largely prohibited.

This enables to direct light emitted by the fluorophores onto the detector, including the light around the sharp emission peak close to the critical angle as is described in the afore mentioned document by E. H. Hellen et al., "*Fluorescence emission at dielectric and metal-film interfaces*", *J. Opt. Soc. Am. B*, Vol. 4, No. 3, p. 337 (1987). Using efficient light collection, the detected signal will be increased without necessary increasing the background.

In another embodiment of the present invention for frontsurface excitation and front surface readout the excitation light needs to be effectively separated from the emitted light. In order to realize this, and additional requirement is added to the optimization target: For the excitation light condition, the medium of incidence for the excitation light is air. The angle of incidence is supposed to be 0°. The excitation light need to be transmitted through the intermediate dielectric layer system to the support 43 in order to be separated form the emitted light.

FIGS. 4a and 4b show the calculated transmission spectrum for an intermediate multilayer stack optimized for efficient light collection for Cy3-Dye and efficient transmission of the excitation wavelength of 532 nm. FIG. 4a indicates the transmission of a wavelength interval around the excitation wavelength for normal incidence coming from air. The broken line in the FIG. 4a indicates the position of the excitation wavelength. FIG. 4b shows the transmission of the excited light for three different angles of incidence.

Thus, the signal/background can be improved by directing the excitation light away from the detector. In a laserscanner readout scheme, as illustrated in FIG. 1, this is realized by adapting the optical properties of the intermediate layer system that almost all excitation light is transmitted through the support and reflections back into the optical path back to the detector are strongly reduced, which leads to reduced background, hence an improved signal/background value.

A severe drawback of most devices mentioned in prior art is that the signal enhancement or improvement of the signal/background can be realized for only one fluorescent molecule, i.e. one wavelength at a time. With the present invention, devices with the above mentioned optical properties of being highly reflective for the emission light and highly transmissive for the excitation light, can be realized for more than one fluorescent dye. For DNA microarrays the most commonly used fluorescent dyes are Cy3 and Cy5 (both registered trademarks by Amersham Inc.).

The required spectral properties for the above described device with a dielectric layer stack are also listed in the table below.

Sample Parameters for efficient light collection are:

Emission wavelength for Cy5-Dye: 650 nm-700 nm (typical fluorescence filter)

Emission wavelength for Cy3-Dye: 550 nm-600 nm (typical fluorescence filter)

Reflective for the emission wavelength for angles of −70° . . . 70°; especially around the critical angle: 40° . . . 60° (s-polarization and p-polarization)

Sample Parameters for reduction of signal/noise are:

Excitation wavelength of Cy5-Dye: 633 nm (e.g. HeNe-Laser)

Excitation wavelength of Cy3-Dye: 532 nm (e.g. YAG-Laser, frequency doubled)

High transmission for the excitation wavelength for angles of −10° . . . 10° (s-polarization and/or p-polarization Based on these spectral parameters and by the use of commercially available thin film design software, such as Filmstar, it is a well known procedure to one skilled in the art to translate the spectral properties into a thin film design for the dielectric layer stack.

Figure 5:
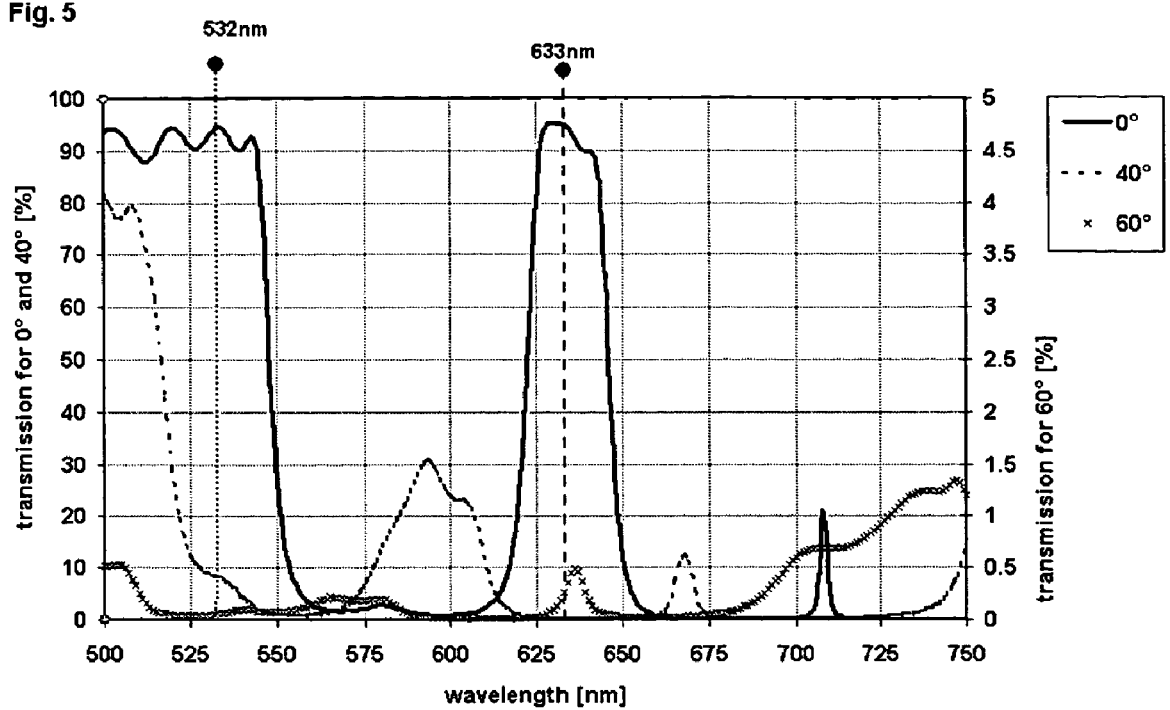
FIG. 5 shows an example of measured optical characteristics of a dielectric layer stack according to the invention.

An example of the measured optical characteristics of a dielectric layer stack that fulfils the requirements is given in FIG. 5. As transparent support, a Schott AF45 glass has been used and as layer materials for the intermediate layer system $NbO_2$ and $SiO_2$ have been choosen. It can be advantageous that the last layer of the intermediate layer system is a chemically reactive material for binding the specific biological sample thereto. For example $SiO_2$ might be preferred in contrast to $NbO_2$ since various protocols exist to apply the linker chemistry to its surface, such as functionalized silanes. This can be taken into account during the design optimization process.

The intermediate layer system can be realized for example by one of the following methods: vapor deposition, replication, transfer, film deposition, by processes of the CVD type (LPCVD, PECVD etc.) or of the PVD type such as sputtering, by film transfer, by the sol-gel process. It may be a layer transferred onto the support by one of the following methods: bonding and molecular adhesion.

FIG. 5 illustrates the measured spectral properties of a support coated with the design realized by magnetron sputtering. It can be seen that the excitation light is almost fully transmitted and the emission light is reflected for both fluorescent dyes Cy5 and Cy3.

One example how to use the device according to the present invention as a microarray is described in the following: It first was pretreated with a thin-film of non fluorescent OptoDex® A (OptoDex is a registered trademark by CSEM) chemical layer. Homogeneous coating presumes that all surfaces received the same final cleaning procedure. Afterwards fluorescence labeled polysaccharides, Cy3-OptoDex and Cy5-OptoDex, were printed in separated 20×20 repeat-arrays, in total 400 spots for each dye, using a pin-and-ring printer. In the following example identical print solutions were used for all slides. For comparison of the performance, all data have been compared to bare glass support without a intermediate layer system.

Figure 6:
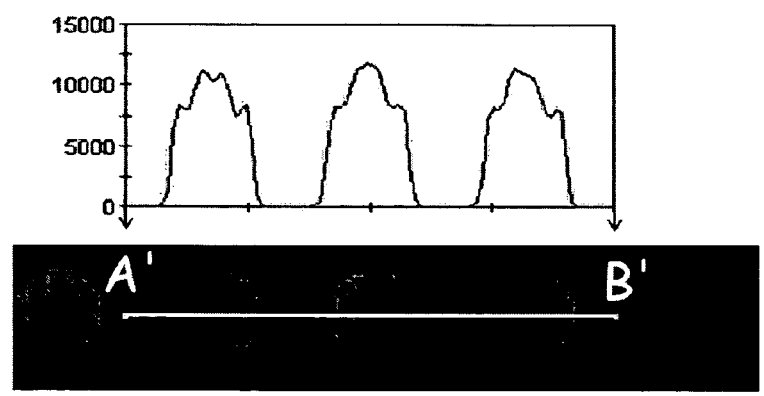
FIG. 6 shows a detail of a scanned image for a bare glass reference device and a measured signal along the line A'B'.
Figure 7:
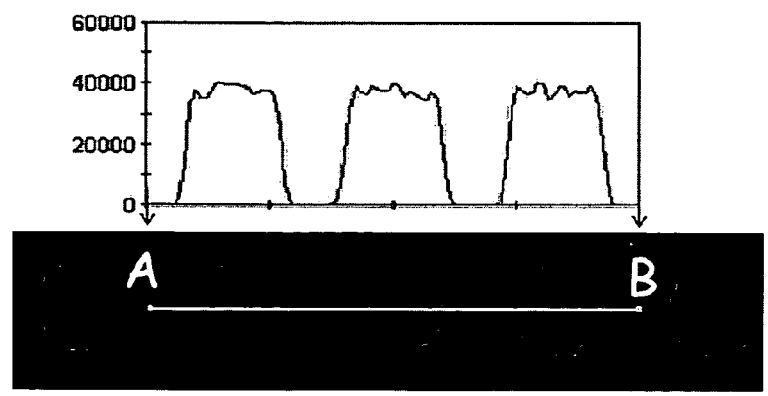
FIG. 7 shows a detail of a scanned image of a device comprising an intermediate layer system according to the present invention and a measured signal along the line AB.

The device has been scanned for Cy3 fluorescent molecules using a commerical laser scanner (Affymetrix 418 Scanner). In FIG. 6 a detail of a scanned image is shown for the bare glass reference device. Shown as well is the measured signal along the line A'B'. The gain setting was at 10. As can be seen the signal is not homogeneous and peaks below 13000. In FIG. 7 a detail of a scanned image of the device comprising an intermediate layer system according to the present invention is shown. Shown as well is the measured signal along the line AB. As can be seen the signal is homogeneous and no characteristic peak appears, the distribution resembles more or less a flat top distribution. In addition the level of the flat top is at about 40000 with a gain setting of 7. As a conclusion if linear gain dependency is assumend the signal of the device according to the present invention is increased by more than a factor of 5.

For comparable Cy5 measurements an increase of more than a factor of 7 was measured.

As mentioned before, the signal/background (S/B) is an other crucial parameter for assessing the performance of such a device. In the table 2, the S/B values are summarized for four different fields, each with 400 spots per device as obtained from the scanner. Typical values for Cy3-dyes are in the range of 390 for a bare glass support, while values are in the range of appr. 2800 for a device with an intermediate layer system. A improvement for the Cy5 S/B values has also been observed as can be seen from the table 2. The performance of two samples according to the present invention (glass 6 multilayer) is compared to the performance of a sample based on a glass support without intermediate layer system.

In this disclosure examples have been discussed how to increase the signal and/or the signal/background values of fluorescence to be measured. Despite the fact that almost all examples given are based on fluorescence, most of the principles can be applied wherever an electromagnetic excitation signal is used and/or an electromagnetic emission signal on an areal sample is to be measured. This includes for example as well phosphorescence and luminescence in general.

In addition it should be stated that many of the principles of the present invention can be used in combination with other methods for improving the signal to be measured. This is especially true for the method to increase the excitation light with the help of dielectric multilayer coatings as disclosed in another application by the same applicant. Here the excitation light is reflected and the areal sample is positioned in the antinode of the resulting standing wave.

It is further possible to combine the principles of the present invention with the evanescent field excitations. In case a waveguide for the excitation light is used for establishing an evanescent field at the location of the areal sample, the waveguide thickness can be chosen small enough in order not to support waveguiding for the fluorescent light. The intermediate layer system according to the present invention can then be used to effectively reflect the emitted light up to the detector (for front surface readout) or effectively transmit the fluorescent light (for rear surface readout). If resonant gratings are used to establish an excitation evanescent field in most cases these resonant gratings show abnormal reflection. Here as well the discussed principle of effectively collecting the fluorescent light and the principle to separate excitation light from emitted light can be used to improve the quality of the measured signal.

TABLE 1

| layer number | Index of refraction | thickness [nm] |
|---|---|---|
| 1 | 2.4 | 61.63 |
| 2 | 1.48 | 121.64 |
| 3 | 2.4 | 11.73 |
| 4 | 1.48 | 132.49 |
| 5 | 2.4 | 62.33 |
| 6 | 1.48 | 127.92 |
| 7 | 2.4 | 16.68 |
| 8 | 1.48 | 111.76 |
| 9 | 2.4 | 65.51 |
| 10 | 1.48 | 102.14 |
| 11 | 2.4 | 70.25 |
| 12 | 1.48 | 100.4 |
| 13 | 2.4 | 71.51 |
| 14 | 1.48 | 99.89 |
| 15 | 2.4 | 71.86 |
| 16 | 1.48 | 99.93 |
| 17 | 2.4 | 71.72 |
| 18 | 1.48 | 100.66 |
| 19 | 2.4 | 71.09 |
| 20 | 1.48 | 103.65 |
| 21 | 2.4 | 69.74 |

TABLE 2

| | Gain setting = 5 | | | |
|---|---|---|---|---|
| Slide Type | Cy3 (S/B) | | Cy5 (S/B) | |
| Reference: Glass | Field 1 | 351 | Field 1 | 35 |
| | Field 2 | 398 | Field 2 | 67 |
| | Field 3 | 393 | Field 3 | 51 |
| | Field 4 | 397 | Field 4 | 86 |
| Glass & Multilayer | Field 1 | 2327 | Field 1 | 215 |
| | Field 2 | 2103 | Field 2 | 232 |
| | Field 3 | 2161 | Field 3 | 231 |
| | Field 4 | 2442 | Field 4 | 271 |
| Glass & Multilayer | Field 1 | 2796 | Field 1 | 187 |
| | Field 2 | 2833 | Field 2 | 191 |
| | Field 3 | 2821 | Field 3 | 193 |
| | Field 4 | 2886 | Field 4 | 207 |

What is claimed is:

1. A sample substrate adapted for use with electromagnetic excitation light directed to a fluorescent sample material disposed on the substrate, causing light to be emitted from the sample, comprising a base and a layer system, the layer system comprising a dielectric multilayer interference coating with at least two layers wherein thicknesses of the layers cause separation of the excitation light from the emitted light;
   wherein the thicknesses of the layers are chosen in such a way that for s-polarized light impinging on the layer system and having a wavelength corresponding to a wavelength of the emitted light and a medium of incidence of the light having an index of refraction of 1.4, less than 1.5% of light is transmitted for angles of incidence from −70 degrees to +70 degrees.

2. The substrate according to claim 1 wherein the emitted light is adapted to be received by a photodetector on a front side of the fluorescent sample material opposite the substrate and the thicknesses of the layers cause reflection of substantially all of the emitted light.

3. The substrate according to claim 2 wherein the thicknesses of the layers cause reflection of the emitted light in two different wavelength bands.

4. The substrate according to claim 2, wherein the thicknesses of the layers cause reflection of the emitted light in two different wavelength bands, wherein one wavelength band ranges from 550 nm to 600 nm and another wavelength band ranges from 650 nm to 700 nm.

5. The substrate according to claim 2, wherein the thicknesses of the layers cause reflection of the emitted light in two different wavelength bands and wherein the thicknesses of the layers cause transmission of not absorbed excitation light for two different excitation wavelengths.

6. The substrate according to claim 2, wherein the thicknesses of the layers cause reflection of the emitted light in two different wavelength bands, wherein one wavelength band ranges from 550 nm to 600 nm and another wavelength band ranges from 650 nm to 700 nm
and wherein the thicknesses of the layers cause transmission of the excitation light for a first and a second excitation wavelength, wherein said first excitation wavelength is within the wavelength range of 532 nm to 548 nm and said second excitation wavelength is around 633 nm.

7. The substrate according to claim 2 where in the excitation light is waveguided within the layer system.

8. The substrate according to claim 7 wherein the emitted light is not waveguided within the layer system.

9. The substrate according to claim 2 wherein the excitation light is received at a front side of the fluorescent sample material opposite the substrate and the thicknesses of the layers cause transmission of substantially all of the excitation light which is not absorbed by the fluorescent sample material.

10. The substrate according to claim 9 wherein the thicknesses of the layers cause transmission of the excitation light in two different wavelength bands.

11. The substrate according to claim 1 wherein the excitation light is received at a front side of the fluorescent sample material opposite the substrate and the thicknesses of the layers cause reflection of substantially all of the excitation light.

12. The substrate according to claim 11 wherein the thicknesses of the layers cause reflection of the excitation light in two different wavelength bands.

13. The substrate according to claim 11 wherein the emitted light is adapted to be received by a photodetector on a rear side of the sample adjacent the substrate and the thicknesses of the layers cause transmission of substantially all of the emitted light.

14. The substrate according to claim 13 wherein the thicknesses of the layers cause transmission of the emitted light in two different wavelength bands.

15. The substrate according to claim 1 wherein the excitation light is received at a rear side of the fluorescent sample material adjacent the substrate and the thicknesses of the layers cause transmission of substantially all of the excitation light.

16. The substrate according to claim 15 wherein the thicknesses of the layers cause transmission of the excitation light in two different wavelength bands.

17. The substrate according to claim 15 wherein the emitted light is adapted to be received by a photodetector on a rear side of the sample adjacent the substrate and the thicknesses of the layers cause transmission of substantially all of the emitted light.

18. The substrate according to claim 17 wherein the thicknesses of the layers cause transmission of the emitted light in two different wavelength bands.

19. The substrate of claim 1 wherein the multilayer interference coating comprises dielectric layers having alternately relatively higher and lower refractive indices such that an outermost layer is one of the layers having a relatively lower refractive index.

20. The substrate of claim 19 wherein the layers comprise at least one of Nb2O5, SiO2, aluminum oxide, magnesium oxide; oxides of the groups VIb, Vb, IVb, scandium, yttrium, calcium, strontium, zinc, iron, indium, tin, cerium, or holmium; oxides of mixtures or alloys of scandium, yttrium, calcium, strontium, zinc, iron, indium, tin, cerium, or holmium; and oxynitrides of Ti, Ta, Zr, Si, Hf, or Al; fluorides of magnesium, barium, strontium, calcium, rare earths, and lead.

21. The substrate of claim 19 wherein the layers comprise Nb2O5 and SiO2.

22. The substrate of claim 1 further comprising a linking coating disposed on an outermost layer of the layer system.

23. The substrate of claim 22 wherein the linking coating layer is biologically active.

24. The substrate of claim 1 wherein the base is rigid.

25. The substrate of claim 1 wherein the base comprises one of glass, plastic, metal, or semiconductor material.

26. A bioanalysis system comprising the substrate according to claim 1.

27. A fluorescence imaging system comprising a sample substrate according to claim 1 and a light source directed to the sample material on said sample substrate, said light including the electromagnetic excitation wavelength and being particular to a specified electromagnetic constituent of said sample material.

28. A laser scanner comprising an electromagnetic imaging system according to claim 27.

29. A sample substrate adapted for use with electromagnetic excitation light directed to a fluorescent sample material disposed on the substrate, causing light to be emitted from the sample, comprising a base and a layer system, the layer system comprising a dielectric multilayer interference coating with at least two layers wherein thicknesses of the layers cause separation of the excitation light from the emitted light;

wherein the emitted light is adapted to be received by a photodetector on a front side of the fluorescent sample material opposite the substrate and the thicknesses of the layers cause reflection of substantially all of the emitted light;

wherein the excitation light is received at a front side of the fluorescent sample material opposite the substrate and the thicknesses of the layers cause transmission of substantially all of the excitation light which is not absorbed by the fluorescent sample material; and wherein greater than 90% of the excitation light which is not absorbed by the fluorescent sample material is transmitted at a 0 degree angle of incidence.

30. A method of manufacturing a sample substrate adapted to obtain electromagnetic emission from a sample disposed on the substrate when the sample is excited by a light comprising the steps of:

selecting at least two dielectric layers of a reflecting dielectric multilayer interference coating;
determining thicknesses of the layers to cause separation of the excitation light from the emitted light wherein the thicknesses of the layers are chosen in such a way that for s-polarized light impinging on the layer system and having a wavelength corresponding to a wavelength of the emitted light and a medium of incidence of the light having an index of refraction of 1.4, less than 1.5% of light is transmitted for angles of incidence from −70 degrees to +70 degrees;

and depositing the layers on a base.

31. The method of claim 30 further comprising the step of depositing a linking coating on the first layer system.

* * * * *